US005728569A

United States Patent [19]
Schrier

[11] Patent Number: 5,728,569
[45] Date of Patent: *Mar. 17, 1998

[54] CHICKEN ANAEMIA AGENT VACCINE

[75] Inventor: Carla Christina Schrier, Boxmeer, Netherlands

[73] Assignee: Akzo Nobel N.V., Arnhem, Netherlands

[*] Notice: The portion of the term of this patent subsequent to Nov. 11, 2011, has been disclaimed.

[21] Appl. No.: 300,688

[22] Filed: Sep. 2, 1994

Related U.S. Application Data

[63] Continuation of Ser. No. 947,198, Sep. 18, 1992, abandoned.

[30] Foreign Application Priority Data

Sep. 20, 1991 [EP] European Pat. Off. ............... 91202452

[51] Int. Cl.$^6$ .................... C12N 7/01; C12N 7/02; C12N 7/06; C12N 7/08; A61K 39/12
[52] U.S. Cl. .................... 435/235.1; 435/236; 435/237; 435/238; 435/239; 424/204.1; 424/816; 424/201.1; 424/202.1
[58] Field of Search ................... 435/235.1, 236, 435/237, 238, 239; 424/204.1, 816, 201.1, 202.1

[56] References Cited

U.S. PATENT DOCUMENTS 3,616,262 10/1971 Coady-Broomall et al. .
4,235,876 11/1980 Gits et al. .
4,530,831 7/1985 Lutticken et al. .

OTHER PUBLICATIONS

Todd et al. J. Gen Virol. 71:819–823 Apr. 1, 1990.
McNulty et al. Avian Pathology 19(1):167–71 (1990).
Bulow et al., J.Vet Med B 33: 568–573, 1986.
McNulty et al., Avian Diseases, vol. 35, pp. 263–268, 1991.
Engstrom et al., Avian Pathology, vol. 17, pp. 33–50, 1988.
Otaki et al., Avian Pathology, vol. 21, pp. 147–151, 1992.
Yuasa et al., Avian Diseases, vol. 23, pp. 366–385, 1979.
Lamichhane, C.M., et al. Avian Diseases 35:515–522 Jul.–Sep. 1991.
Lucio, B. et al. Avian Diseases 34:146–153 1990.
McNulty, M. S. Avian Pathology 20:187–203 1991 (publicly available Jul. 1991).
V.V. Bulow, et al., "Propagation of Chicken Anaemia Agent (CAA) in Chicken embryos," Journal of Veterinary Medicine, Series B, vol. 33, No. 9, 1986, Germany, pp. 664–669.
V.V. Bulow et al., "Attenuation of Chicken Anaemia Agent by Serial Passages in Cell Culture," Biological Abstracts, vol. 83, No. 6, p. Ab–480, Abstract No. 54426, 1987, USA.
E. Vielitz, "Anemia in Broilers: Development of a Vaccine for Parent Stock," Journal of Veterinary Medicine, Series B, vol. 34, No. 8, pp. 553–557, Oct. 1987, Germany.

Primary Examiner—Anthony C. Caputa
Attorney, Agent, or Firm—Mary E. Gormley

[57] ABSTRACT

The present invention provides a live and inactivated Chicken Anaemia Agent vaccine capable of evoking an immune response in a vaccinated chicken. The CAA virus of the vaccine is attenuated by serial passages in embryonated eggs.

20 Claims, No Drawings

CHICKEN ANAEMIA AGENT VACCINE

This is a continuation of application Ser. No. 07/947,198 filed Sep. 18, 1992, now abandoned.

BACKGROUND OF THE INVENTION

The present invention is concerned with a vaccine for the protection of poultry against Chicken Anaemia Agent (CAA), either live or inactivated, a method for the preparation of such a vaccine, a method for the preparation of CAA virus product as well as with a microbiologically pure composition of CAA viruses.

Chicken anaemia agent (CAA) is the causative agent of avian infectious anaemia and was first described by Yuasa et al. in 1979 (Avian Diseases 23, 366–385, 1979).

In young susceptible chickens CAA produces marked anaemia with aplasia/hypoplasia of the bonemarrow and atrophy of the thymus.

Chickens develop an age resistance to experimentally induced disease due to CAA. This is essentially complete by the age of 2 weeks, but older birds are still susceptible to infection (Yuasa, N. et al., 1979 supra; Yuasa, N. et al., Avian Diseases 24, 202–209, 1980). However, if chickens are dually infected with CAA and an immunosuppressive agent (IBDV, MDV etc.) age resistance against the disease is delayed (Yuasa, N. et al., 1979 and 1980 supra; Bülow von V. et al., J. Veterinary Medicine 33, 93–116, 1986). Morbidity and mortality in chickens inoculated with CAA are strongly related with the dose of CAA used for inoculation; that is, the larger the dose, the higher the severity of the disease (Yuasa, N. et al., 1979 supra).

CAA does not grow in standard cultured monolayer cells derived from a variety of chicken and chicken embryo tissues, such as chicken embryo fibroblasts (CEF), chicken embryo brain cells, chicken embryo liver cells and chicken cells derived from kidney, thymus, Bursa of Fabricius, bone marrow or white blood cells (Yuasa, N. et al., 1979 supra; Yuasa, N., Natl. Inst. Anim. Health Q., 23, 13–20, 1989), nor does it grow in a variety of commonly used mammalian cell lines such as VERO, CRFK, MDCK and A-72 (Rosenberger, J. K. and Cloud, S. S., Avian Diseases 33, 707–713, 1989). CAA does grow in some lymphoblastoid cell lines established from Marek's disease and lymphoid leukosis lymphomas, especially in MDCC-MSB1 cell culture (Yuasa, N., 1983 supra). However, disadvantageously, CAA grows to comparatively low titres in MDCC-MSB1 cells. Titres of only $10^{5.0}$ to $10^{6.0}$ $TCID_{50}/0.1$ ml in MDCC-MSB1 cells could be obtained. Additionally it was found that CAA multiplied in MDCC-MSB1 cells to only about 10 times the inoculated dose (Yuasa, N., 1983 supra, Bülow von, V. et al., Zentralblatt Vet. Med. 32, 679–693, 1985).

In addition to chickens, CAA can also be propagated in chicken embryos (Yuasa, N. and Yoshida, I., Natl. Inst. Anim. Health Q. 23, 99–100, 1983; Bülow von, V. and Witt, M., J. Vet. Med. 33, 664–669, 1986). However, no lethal or pathological effects could be seen for these embryos indicating that CAA does not propagate in embryonated eggs to amounts large enough to affect the embryos. The highest titres of CAA that could be obtained from whole embryos varied between $10^{5.0}$ to $10^{6.5}$ $TCID_{50}/ml$ as assayed in MDCC-MSB1 cells which equal the titres obtained from liver extracts of experimentally infected chickens.

Bülow von, V. and Witt, M. (supra) studied the propagation of virulent CAA in embryonated eggs as a means for production of live vaccines which can be administered to parent stock requiring no attenuation of the viruses. However, it is mentioned therein that attenuation of the viruses has to be prevented, because this may lead to loss of immunogenicity (Bülow von, V. and Fuchs, B., J. Vet. Med. 33, 568–573, 1986).

Bülow and Fuchs (J. Vet. Med. 33, 568–573, 1986) reported that the pathogenicity of CAA strain Cux-1 was decreased after 12 serial passages in MDCC-MSB1 cells, however, no data with respect to the immunogenicity of these less pathogenic strains is disclosed therein. In fact reduction of the immunizing potency with the reduction of the pathogenicity is anticipated by Bülow and Fuchs.

Neither Yuasa (1983 supra) nor Goryo et al. (Avian Pathology 16, 149–163, 1987) nor Otaki et al. (Avian Pathology 17, 333–347, 1988) found evidence at all for attenuation on MDCC-MSB1 cells after 19 passages of the Gifu-1 strain, 40 passages of the TK-5803 strain and 40 passages of the CAA82-2 strain, respectively.

Vielitz E. et al. (J. Vet. Med. 34, 533–557, 1987) report the evaluation of a live CAA vaccine derived from the Cux-1 strain. However, no attenuated CAA strain is used therein. This vaccine comprising virulent CAA is administered to 9–15 weeks old chickens and showed no pathogenicity in the inoculated birds. In view of the known age resistance to experimentally induced disease due to CAA, which is essentially complete by the age of 2 weeks, the level of attenuation of the live vaccine virus for the inoculated birds themselves is of less importance in this case. However, in order to prevent pathological signs in young chicks after contact with live CAA vaccine, the live CAA vaccine virus should be attenuated significantly.

An alternative for a live CAA vaccine would be an inactivated adjuvanted vaccine. Such an inactivated vaccine could also be used to boost existing immunity in chickens. However, no inactivated CAA vaccine has been reported up to now because this approach is complicated by the present inability to grow the CAA virus to high titres in vitro (McNulty, M. S., Avian Pathology 20, 187–203, 1991).

BRIEF DESCRIPTION OF THE INVENTION

Therefore, a first object of the present invention is to provide CAA viruses which can be propagated to high titers in vitro.

A further, object of the present invention is to provide a CAA vaccine derived from a CAA virus strain displaying significant decreased pathogenicity in young chicks with respect to the field isolates but retaining its immunogenicity.

Furthermore, it is an object of the invention to provide an inactivated CAA vaccine comprising sufficiently high amounts of CAA antigen to evoke an immune response in chickens after vaccination.

In addition it is an object of the present invention to provide a universal process for the attenuation of CAA virus strains.

The present invention is a new CAA virus, a CAA virus capable of inducing lesions in chicken embryos, and which can be grown to high titers, thereby making them suitable for use in vaccine preparations. A strain of this virus is known as I-1141 and has been deposited with the CNCM of the Institute Pasteur in France.

DETAILED DESCRIPTION OF THE INVENTION

The present invention relates to new CAA viruses, i.e. CAA viruses which are able to induce lesions in chicken embryos. Lesions due to CAA include mortality, pale embryos and haemorrhages, especially of the head. These type of CAA viruses display several advantageous properties. One of the favourable characteristics of the CAA viruses according to the invention is that they can be grown to high titers in vitro as is outlined in detail below.

A further advantage of said CAA viruses is that these viruses although more virulent for chicken embryos have a reduced pathogenicity for one-day-old ckicks if compared to CAA field viruses but retained their immunogenic properties.

Preferably, the invention is directed to CAA viruses of the strain I-1141 (19th passage level) deposited on Sep. 12, 1991 with the Collection Nationale de Cultures de Microorganismes of the Institut Pasteur, 25, Rue de Docteur Roux, 75724 Paris Cedex 15, France. These viruses can be cultured in embryonated eggs to a titer of at least $10^{8.4}$ $TCID_{50}$/ml, and in addition are less pathogenic to one-day-old chickens than the parent field strain, yet are as immunogenic as the parent strain.

The new class of CAA viruses can be obtained by passaging any available CAA virus in embryonated eggs as described below and in the Examples.

A novel vaccine for the protection of poultry against CAA is characterized in that the vaccine comprises CAA viruses which are able to induce lesions in chicken embryos, preferably these viruses are obtained by means of passaging in embryonated eggs.

After isolation of an available CAA strain from chicken tissue, e.g. the liver, the tissue homogenate can be used in a multi-step attenuation process. First, if desired the CAA virus can be passaged and propagated in a tissue or cell culture suited for CAA, such as in MDCC-MSB1 cells, before inoculation into eggs. This virus stock can then be used to infect embryonated eggs and subsequent propagation and passaging of the virus in embryonated eggs by methods known in the art for this purpose.

More in particular, eggs are infected with CAA via the yolk sac route with at least $10^{4.5}$ $TCID_{50}$ per egg according to standard procedures. Infected embryos are harvested after about 13 days post-inoculation, homogenized and diluted with for example tryptose 2.5% (1:20 v/v). Subsequently, fresh embryonated eggs are inoculated with 0.2 ml of the homogenate per egg in each egg passage step. Following the last egg passage, virus is propagated and subsequently harvested and processed into a vaccine with immunizing activity against CAA infection. The virus of the last passage can be propagated in embryonated eggs or in a cell or tissue culture susceptible for CAA, such as MDCC-MSB1 cells. In the case of embryonated eggs the embryos and/or the membranes and/or the allantoic fluids are harvested.

The number of egg-passages which are necessary to obtain CAA viruses with the favourable growth and attenuated properties is inter alia dependent on the specific CAA strain and the level of attenuation and/or in vitro titre desired.

A typical number of total egg passages of CAA viruses which results in viruses with a significant decrease of the pathogenicity suited to prepare a live vaccine according to the invention is 18 or more and is preferably 34 or more.

In particular, the vaccine according to the invention is derived from viruses of the Intervet CAA strain 26P4. This strain was originally isolated from the livers of chickens in the field suffering from anaemia. After isolation, this strain was passaged 5 times in MDCC-MSB1 cells and subsequently passaged 19 times in embryonated eggs. A sample of this strain has been deposited with the Collection Nationale de Cultures de Micro-organismes (CNCM) of the Institut Pasteur at Paris, France under the accession number I-1141. It is clear that not only CAA viruses of the 19th passage level can be used for the preparation of a vaccine according to the invention, also viruses of subsequent passage levels of this strain are well suited.

This attenuated strain displays a significant decrease of its pathogenicity whereas the immunogenic properties of the viruses of this strain are unaffected as measured with the virus neutralisation (VN) test, with respect to the non-egg adapted viruses of this strain.

The new live CAA viruses obtainable according to the process described above have several distinguishing characteristics, in particular the CAA viruses induce lesions specific for CAA including lethal and/or pathological effects in embryos as opposed to all CAA strains disclosed up to now (Yuasa, N. et al., 1979 supra; Yuasa, N. and Yoshida, I., 1983 supra; Bülow von, V. and Witt, M., 1986 supra).

Other, favourable characteristics are:

the CAA viruses are attenuated, i.e. induce significantly less pathological symptoms with respect to CAA isolated from the field when administered to day-old SPF chickens;

the CAA viruses are adapted to growth in embryonated eggs to high titers.

The vaccine according to the invention containing live attenuated CAA can be prepared and marketed in the form of a suspension or as a lyophilized product in a manner known per se.

For live vaccines the dose rate per chick may range from $10^{1.0}$ to $10^{7.0}$ $TCID_{50}$ of the attenuated virus.

It is advantageous to add a stabilizer, particularly if a dry composition is prepared by lyophilization. Suitable stabilizers are, for example, SPGA (Bovarnik et al., J. Bacteriology 59, 509, 950), carbohydrates (such as sorbitol, mannitol, starch, sucrose, dextran or glucose), proteins (such as albumin or casein), or degradation products thereof, and buffers (such as alkali metal phosphates). If desired, one or more compounds with adjuvant activity can also be added. Suitable compounds for this purpose are, for example, vitamin-E acetate o/w -emulsion, aluminium hydroxide, phosphate or oxide, mineral oil (such as Bayol F®, Marcol 52®) and saponins.

Another important aspect of this invention is the use of an inactivated CAA vaccine for the prevention of the disease in chickens caused by this pathogen. Up to now no inactivated CAA vaccine could be prepared which evoked an immune response in inoculated chickens.

The present invention for the first time provides an inactivated CAA vaccine comprising an effective amount of CAA viruses, which vaccine is capable of eliciting the production of CAA virus neutralizing antibodies in a chicken after vaccination.

In particular the inactivated vaccine is derived from the new class of CAA viruses according to the present invention.

A preferred inactivated CAA vaccine according to the invention includes one or more isolates of inactivated CAA which have been attenuated in embryonated eggs by serial passages as described above. If desired, the egg adapted CAA may be propagated in a susceptible cell or tissue culture, such as MDCC-MSB1 cells, before the inactivation process.

Preferably, this inactivated vaccine comprises CAA having a pre-inactivation virus titre of greater than about $10^{7.5}$ $TCID_{50}$ per dose, preferably greater than about $10^{8.0}$ $TCID_{50}$ per dose and more preferred greater than about $10^{9.0}$ $TCID_{50}$ per dose as assayed on MDCC-MSB1 cells.

Inactivated CAA fluids may also be concentrated by any number of available techniques such as an Amicon concentrating device, precipitation techniques, such as with polyethylene glycol, concentration by means of ultracentrifugation or adjuvant concentration techniques.

The aim of inactivation of the CAA viruses is to eliminate reproduction of the viruses. In general, this can be achieved by chemical or physical means. Chemical inactivation can be effected by treating the viruses with, for example, enzymes, formaldehyde, β-propiolactone, ethylene-imine or a derivative thereof. If necessary, the inactivating compound is neutralized afterwards; material inactivated with formaldehyde can, for example, be neutralized with thiosulphate. Physical inactivation can preferably be carried out by subjecting the viruses to energy-rich radiation, such as UV light, X-radiation or γ-radiation. If desired, the pH can be brought back to a value of about 7 after treatment.

Usually, an adjuvant (for example such as mentioned above), and, if desired, one or more emulsifiers, such as Tween® and Span®, are also added to the inactivated material.

The vaccine according to the invention is administered in an effective dosage of the virus material, i.e. the amount of virus material that will induce an immune response in a chicken against CAA.

Vaccines according to the invention may be administered by spray, eye drop, nose drop, orally (e.g. drinking water), or by means of intramuscular or subcutaneous injection at any age.

A vaccine according to the invention, live or inactivated, can be prepared from any CAA strain available or obtainable from chickens suffering from infection with this pathogen. A number of CAA isolates have been described already in the prior art, e.g. the Cux-1 strain (Bülow von, V. et al., J. Veterinary Medicine 30, 742–750, 1983), the Gifu-1 strain (Yuasa, N. et al., 1979 supra), the TK-5803 strain (Goryo, M. et al., 1987 supra) and the CAA82-2 strain (Otaki et al., 1988 supra).

Preferably, a vaccine according to the invention, live or inactivated, is derived from viruses of the Intervet CAA strain 26P4 deposited at the CNCM under accession number I-1141.

Vaccines according to the present invention, preferably the vaccine containing the inactivated CAA, may contain combinations of the CAA component and one or more unrelated avian viruses, preferably Newcastle Disease virus (NDV), Infectious Bronchitis virus (IBV), Infectious Bursal Disease virus (IBDV), Marek's Disease virus (MDV), Herpes virus of Turkey's (HVT), Infectious Laryngotrachetis virus or other avian herpes viruses, Reo virus, Egg Drop Syndrome virus, Avian Encephalomyelitis virus, Reticuloendotheleisis virus, Leucosis virus, Fowlpox virus, Turkey Rhinotracheitis virus (TRTV) or Adeno virus.

Another important aspect of the present invention is the new production system for CAA virus product. The resulting virus product can be used to formulate a vaccine composition for the combating of CAA infection in poultry. Until the present invention maximal titres which could be obtained from in vitro propagation varied between about $10^{6.0}$–$10^{7.0}$ $TCDI_{50}$/ml. The inability of obtaining satisfactory levels of CAA antigen by the present production systems at an acceptable price has not been overcome yet in the prior art. Moreover, the present inability to grow the CAA virus to high titres has prevented the preparation of an inactivated CAA vaccine, requiring a high concentration of antigen.

The method for the preparation of CAA virus product according to the present invention includes the steps of inoculating a susceptible substrate with CAA viruses which are able to induce lesions in chicken embryos, in particular with such CAA viruses which have been attenuated in embryonated eggs, propagating the CAA and harvesting CAA containing material.

Preferably, the substrate on which these CAA viruses are propagated are SPF embryonated eggs. Embryonated eggs can be inoculated with for example 0.2 ml CAA containing suspension or homogenate comprising at least $10^{4.5}$ $TCID_{50}$ per egg. Preferably, eggs are inoculated with about $10^{6.0}$ $TCID_{50}$ and subsequently incubated at 100° F. for 13 days. After 13 days the CAA virus product can be harvested by collecting the embryo's and/or the membranes and/or the allantoic fluid and appropriate homogenizing this material. The homogenate can be centrifuged thereafter for 10 min. at 2500 g followed by filtering the supernatant through a filter (100 μm).

Alternatively, the above-mentioned CAA viruses can be inoculated onto a susceptible cell culture, e.g. MDCC-MSB1 cells, followed by cultivation of the cells and collecting the propagated virus.

Harvestable virus titres of at least about $10^{8.0}$ $TCID_{50}$/ml and usually at least about $10^{8.4}$ as assayed in MDCC-MSB1 cells can be obtained after 10–18 days post-inoculation, preferably 13 days after inoculation. The harvested fluids can be combined with a virus stabilizer as described before for final product filling and/or frozen in bulk or freeze-dried.

Alternatively, the harvested fluids may be inactivated. CAA fluids can be inactivated with a number of inactivating agents such as, but not limited to, binary ethylenimine, acetyl ethylenimine, β-propiolactone at concentrations of 0.1 to 0.5% are preferably used. The inactivating agent can be added to the virus contained in the homogenate or filtrate thereof.

β-propiolactone is added to the virus fluids, with the adverse shift in pH to acidity being controlled with sodium hydroxide or sodium bicarbonate solution. The combined inactivating agent-virus fluids are incubated at temperatures from 4° C. to 37° C. Incubation times of 1 to 72 hours may be used.

Furthermore, the invention comprises a method for controlling CAA infection in poultry, comprising administering a vaccine prepared from viruses of a CAA strain attenuated in embryonated eggs. This method includes the administration of live or inactivated vaccines.

EXAMPLE 1

Attenuation of CAA in embryonated eggs

The original Intervet strain 26P4 was isolated from the livers of chickens in the field suffering from anaemia (exp. VIM-CA-89-4-153). After isolation the strain was passaged 5 times in MDCC-MSB1 cells before inoculation into eggs. Eggs were inoculated into the yolk sac with 0.2 ml CAA strain 26P4 or Gifu (Yuasa, N. et al., Avian Diseases 23, 366–385, 1979). After 13 days incubation at 100° F. (relative humidity: 55%) embryos were harvested and homogenized. The homogenate was centrifuged for 10 minutes at 2500 g. Supernatant was harvested and poured through a 100 μm filter. The homogenate was diluted at 1:20 in tryptose 2.5% and 0.2 ml per egg was inoculated. By doing so, more than 19 passages were made with strain 26P4. A sample of the 19th egg passage of this strain (CAA Masterseed 18-09-1990; 1 ml/fl) has been deposited with the CNCM of the Institut Pasteur, Paris, France under accession number I-1141.

The Gifu strain was attenuated by passaging 14 times in embryonated eggs.

EXAMPLE 2

Comparison of growth characteristics in embryonated chicken eggs of two high egg-passage CAA viruses and low egg-passage CAA viruses.

30–60 SPF eggs were inoculated in the yolk sac with viruses of different egg-passage levels. After 7 days incubation at 100° F. (relative humidity 55%) the eggs were candled and the dead embryonated eggs or the non fertilized eggs were discarded.

From the seventh day p.i. on the eggs were candled daily and embryo mortality was recorded.

Recording of embryo-death due to CAA is started on 10 days p.i., i.e. on day 11.

13 days after inoculation the embryos were harvested homogenized and centrifuged at 2500 g for 10 minutes. The supernatant was harvested and titrated for virus infectivity in MDCC-MSB1 cells.

Tables 1 and 2 show that the high egg-passage CAA viruses which are able to induce embryo lesions and/or death can be grown in vitro to high titres in comparison with the low egg-passage viruses.

TABLE 1

Growth characteristics in embryonated eggs of strain 26P4

| egg-passage | harvest titre logs $TCID_{50}/ml$ | Embryo-death due to CAA Day 11 | 14 | % of embryo death due to CAA |
|---|---|---|---|---|
| 3 | 7.6 | 1 | 0 | 3.3 |
| 10 | 7.4 | N.D. | N.D. | N.D. |
| 14 | 8.0 | N.D. | N.D. | N.D. |
| 17 | 8.6 | 6 | 2 | 26.6 |
| 19 | 8.4 | N.D. | N.D. | N.D. |
| 24 | 8.4 | N.D. | N.D. | N.D. |
| 33 | 9.3 | 7 | 6 | 21.7 |

N.D. = not determined.

Embryos were harvested at 13 days p.i.

Embryos inoculated with the 3rd egg-passage 26P4 strain didn't show any embryonic lesion.

Embryos inoculated with the 17th egg-passage were pale, and several embryos (especially the dead ones) showed haemorrhages of the head.

TABLE 2

Growth characteristics in embryonated eggs of strain Gifu

| Egg-Passage | harvest titre logs $TCID_{50}$/ml | Embryo-death due to CAA Day 11 | 12 | 13 | 14 | Embryo-lesions due to CAA | % of embryo death and embryo lesions due to CAA |
|---|---|---|---|---|---|---|---|
| 2 | N.D. | 0 | 0 | 0 | 0 | 0 | 0 |
| 3 | 7.0 | 0 | 1 | 0 | 0 | 0 | 3.3 |
| 4 | 7.3 | 0 | 0 | 0 | 0 | 1 | 3.3 |
| 5 | 7.6 | 0 | 1 | 0 | 0 | 1 | 6.6 |
| 6 | 7.6 | 0 | 0 | 0 | 2 | 0 | 6.6 |
| 7 | 7.6 | 0 | 0 | 0 | 0 | 3 | 10.0 |
| 8 | 8.0 | 0 | 0 | 0 | 0 | 4 | 13.3 |
| 9 | 7.4 | 1 | 2 | 0 | 0 | 4 | 11.6 |
| 10 | 8.5 | 0 | 1 | 0 | 1 | 6 | 13.3 |
| 11 | 7.8 | 0 | 0 | 2 | 0 | 5 | 11.6 |
| 12 | 7.8 | 1 | 2 | 0 | 1 | 10 | 23.3 |
| 13 | 8.3 | 3 | 3 | 5 | 0 | 7 | 30.0 |
| 14 | 8.3 | 0 | 3 | 0 | 6 | 11 | 33.3 |

N.D. = not determined

EXAMPLE 3

Experimental vaccination with live CAA vaccines

Experiments were carried out in order to determine the attenuation of the CAA viruses and the retaining of the immunogenicity by passaging the viruses through embryonated eggs.

Pathogenicity of live CAA vaccines

In Experiment 1 the following passage levels of the Intervet strain were used:

1st egg-passage level (low egg-passage level)

18th egg-passage level (high egg-passage level)

embryo homogenate derived from uninfected embryonated SPF eggs (13 days incubation).

In Experiment 2 the following passage levels of the Intervet strain were used:

4th egg-passage level (low egg-passage level)

19th egg-passage level (high egg-passage level) CAA virus of the 19th passage level was layed down as "Master seed"

embryo homogenate derived from uninfected embryonated SPF eggs (13 days incubation).

The viruses were diluted in such a way that 0.2 ml of the diluted CAA strain contained about $10^{6.0}$ $TCID_{50}$. One-day-old SPF chickens were inoculated with 0.2 ml of the vaccine by intramuscular route.

In experiment 3 the following passage levels of the Gifu strain were used:

1st egg-passage

14th egg-passage 107 one-day-old chickens were divided in three groups of 35–36 birds (see above). The third group was not vaccinated (control group).

At 10 and 14 days post-vaccination 10 birds per group were taken out of the isolator for hematocrit determination and necropsy.

3 weeks post-vaccination the birds were bled and sera were examined for CAA-antibodies by indirect immunofluorescence test (IIFT).

Vaccination was carried out as described for experiment 1 and 2.

In Experiment 1 and 2 150 one-day-old SPF chickens were divided in three groups of 50 birds each and each group was placed in a negative pressure isolator.

40 birds per group were vaccinated with one of the above mentioned viruses and 10 birds per group were not vaccinated and served as contact controls.

At 10, 14 and 21 days post-vaccination 4 or 8 birds per group were taken out of the isolator for hematocrit determination and necropsy.

5 weeks post-vaccination the birds were bled and sera were examined for CAA antibodies by the VN-test.

Virus titration.

The virus was titrated in MDCC-MSB1 cells, using 96 well microplates (tissue culture grade).

Serial 10 fold dilutions of the virus were made in RPMI 1640 medium supplemented with 10% fetal calf serum and antibiotics.

Ten wells of a 96 well microplate were filled with 100 µl per well of every virus dilution.

Subsequently 100 µl MDCC-MSB1 cells (end concentration $6\times10^5$ cells per ml) were added.

The cells were subcultured every 2–3 days and the endpoint was read after 10 subcultures. The infectivity titre was calculated according to Reed and Muench (Reed, L. J. and Muench, H., Am. J. Hyg. 27, 493–497, 1938).

Serological test.

Antibodies against CAA were measured by a VN-test employing 96 well microplates using MDCC-MSB1 cells and the conventional constant virus; varying serum method. (Kunitoshi, L., and Yuasa, N., Jpn. J. Vet. Sci. 52, 873–875, 1990).

IIFT was carried out according to standard procedures (Yuasa, N. et al., Avian Pathology 14, 521–530, 1985).

Hematocrit value

Blood was taken from the wing vein into a heparinized microhematocrit capillary tube. The hematocrit value (%) was read after centrifugation at 12.000 rpm for 5 minutes. Chickens were regarded as anaemic when they showed a hematocrit value below 27.0%. (Yuasa, N. et al., 1979 supra).

The main pathological lesions which were induced in the SPF chickens from Experiment 1–3 are summarized in Tables 3–5, respectively.

TABLE 3

Pathogenicity experiment in one-day-old SPF chickens (26P4 strain).

| | Total morbidity in percentage | | | |
|---|---|---|---|---|
| passage level | mortality[1] | TA[2] | PB[3] | Ht (low)[4] |
| 1st egg-passage | 33 | 80 | 65 | 40 |
| 18th egg-passage | 4 | 40 | 40 | 21 |
| contact controls | 0 | 0 | 0 | 0 |
| 1st egg-passage contact controls | 0 | 0 | 0 | 0 |
| 18th egg-passage controls | 0 | 0 | 0 | 0 |

[1] Mortality due to CAA infection, occuring 14–21 days post-inoculation
[2] Total number of birds with thymus atrophy/total number of birds examined × 100%
[3] Total number of birds with pale, fatty bone-marrow/total number of birds examined × 100%
[4] Total number of birds with Ht-value lower than 27%/total number of birds examined × 100%.

TABLE 4

Pathogenicity experiment in one-day-old SPF chickens (26P4 strain).

| | Total morbidity in percentage | | | |
|---|---|---|---|---|
| passage level | mortality[1] | TA[2] | PB[3] | Ht (low)[4] |
| 4th egg-passage | 13 | 70 | 61 | 87 |
| 19th egg-passage | 0 | 33 | 31 | 35 |
| contact controls | 0 | 0 | 0 | 0 |
| 4th egg-passage contact controls | 0 | 0 | 0 | 0 |
| 19th egg-passage controls | 0 | 0 | 0 | 0 |

[1] Mortality due to CAA infection, occuring 14–21 days post-inoculation
[2] Total number of birds with thymus atrophy/total number of birds examined × 100%
[3] Total number of birds with pale, fatty bone-marrow/total number of birds examined × 100%
[4] Total number of birds with Ht-value lower than 27%/total number of birds examined × 100%.

TABLE 5

Pathogenicity experiment in one-day-old SPY chickens (Gifu strain).

| | Total morbidity in percentage | | | | serology |
|---|---|---|---|---|---|
| passage level | mortality[1] | TA[2] | PB[3] | Ht (Low)[4] | titre[5] |
| 1st passage | 44 | 100 | 85 | 85 | 8.3 ± 1.2 |
| 14th passage | 0 | 70 | 60 | 60 | 8.2 ± 1.4 |
| Controls | 0 | 0 | 0 | 0 | ≦4.0 ± 0.0 |

[1]–[4] as described in Table 3
[5] mean log base 2 with standard deviation

There is a marked difference in pathological changes between the low egg-passage viruses and the high-egg passage viruses of both CAA isolates, not only in the total number of birds which were affected but also in the severity of the pathological changes as demonstrated by the difference in mean Ht-value.

Also the gross lesions of the bone-marrow and the thymus induced by the high egg-passage viruses were less severe than the lesions induced by the low egg-passage viruses.

Immunogenicity of live CAA vaccines

Table 5 demonstrates that the immunogenicity of the Gifu strain was not adversely affected as a result of the attenuation of the CAA virus.

In Table 6 the serology results of Experiment 1 and 2 are shown. Despite the decrease of the pathogenic properties of the high egg-passage virus, no decrease of the immunogenicity of this virus was noticed.

TABLE 6

Results of the virus neutralization test 5 weeks post-inoculation.

| | mean VN titre[1] | |
|---|---|---|
| passage level | vaccinated | contact controls |
| 1st egg-passage | 8.7 ± 0.9 | 8.5 ± 1.4 |
| 18th egg-passage | 8.2 ± 1.3 | 7.6 ± 1.5 |
| controls | | <4 |
| 4th egg-passage | ≧10.2 ± 0.6 | ≧10.0 ± 0.8 |
| 19th egg-passage | 9.2 ± 0.9 | ≧10.3 ± 0.6 |
| controls | | <4 |

[1] expressed in log base 2 with standard deviation.

EXAMPLE 4

Vaccination with live combination vaccine

Reo virus vaccine: commercially available (Intervet International B.V., The Netherlands) live Reo vaccine Nobilis® (batch 016901). The vaccine was diluted in a diluent according to the recommendations of the manufacturer.

CAA vaccine: live CAA virus of the 19th egg-passage level of the Intervet strain was diluted in a diluent in such a way that 1 bird dose (0.2 ml) contains $10^{2.6}$ TCID$_{50}$.

Four week old SPF chickens were vaccinated intramuscularly with either 1 bird dose of the live Reo vaccine; 1 bird dose of the live CAA vaccine or with 1 bird dose of a live combined Reo and CAA vaccine.

Four and six weeks post-vaccination blood samples were taken and the sera were tested in the virus neutralization test for the presence of antibodies to CAA and Reo virus (Table 7).

TABLE 7

Results of the virus neutralization test.

| vaccine | mean VN titre[1] | | | |
|---|---|---|---|---|
| | CAA | | Reo virus | |
| | 4 wks.p.v. | 6 wks.p.v. | 4 wks.p.v. | 6 wks.p.v. |
| Reo vaccine | <4.0 ± 0.0 | <4.0 ± 0.0 | 2.3 ± 2.0 | 2.3 ± 1.4 |
| CAA vaccine | ≧9.6 ± 0.8 | ≧9.5 ± 1.2 | <1.0 ± 0.0 | <1.0 ± 0.0 |
| combined vaccine | ≧9.1 ± 1.1 | ≧9.8 ± 1.1 | 3.4 ± 1.8 | 1.5 ± 1.8 |
| controls | <4.0 ± 0.0 | <4.0 ± 0.0 | <1.0 ± 0.0 | <1.0 ± 0.0 |

[1]expressed in log base 2 with standard deviation.

From the table above it is clear that although the combined vaccine contains both virus types in a live form, no adverse mutual interference of their immunogenicity is observed.

EXAMPLE 5

Experimental vaccination with inactivated CAA vaccine

Four weeks old SPF chickens were vaccinated intramuscularly with an inactivated CAA vaccine in a water-in-oil emulsion (w/o). The vaccine was prepared from the embryo homogenate of the 19th egg-passage level of the Intervet strain. The viruses were inactivated with 0.5% β-propiolactone for 3 hours at 37° C. A w/o emulsion was prepared containing 50% inactivated CAA-egg material and 50% mineral oil-emulsion.

0.5 ml of the w/o-emulsion containing $10^{7.5}$ TCID$_{50}$ viral antigen based on infectivity titre was injected intramuscularly per chicken. Eight weeks after the vaccination the birds received a second vaccination intramuscularly with the same inactivated vaccine. At different times after the first and second vaccination blood samples were taken and the sera were tested in the VN test for the presence of CAA-antibodies (Table 8). It is demonstrated that an inactivated vaccine containing $10^{7.5}$ TCID$_{50}$ viral antigen based on infectivity titre is able to induce an immune response in an inoculated animal.

In other vaccination experiments the same strategy was followed as described above except that the vaccine dose was $10^{8.0}$ and $10^{9.0}$ TCID$_{50}$ in 1 ml oil-in-water emulsion (Table 9)

TABLE 8

Results of the virus neutralization test
VN titre[1]

| chicken | weeks after vaccination | | | weeks post booster | | |
|---|---|---|---|---|---|---|
| | 4 wks | 6 wks | 8 wks | 2 wks | 4 wks | 6 wks |
| 801/802 | <4 | <4 | <4 | 6 | 6 | 7 |
| 803/804 | 8 | 7 | N.D. | 9 | 8 | 8 |
| 805/806 | 5 | 4 | 6 | 6 | 6 | 4 |
| 807/808 | 6 | 8 | 9 | 10 | ≧11 | ≧11 |
| 809/810 | 6 | 5 | 4 | 7 | N.D. | 6 |
| 811/812 | 4 | <4 | 4 | 4 | 4 | 4 |
| 813/814 | 4 | <4 | <4 | <4 | <4 | <4 |
| 815/816 | 4 | 4 | 4 | 6 | 6 | 5 |
| 817/818 | <4 | <4 | <4 | 4 | 4 | N.D. |
| 819/820 | <4 | 5 | <4 | 6 | 5 | N.D. |
| 821/822 | <4 | <4 | <4 | 6 | 7 | 6 |
| 823/824 | 6 | 7 | 6 | 8 | 7 | 7 |
| Contact | N.D. | N.D. | <4 | <4 | <4 | <4 |
| Controls | N.D. | N.D. | <4 | <4 | <4 | <4 |
| | N.D. | N.D. | <4 | <4 | N.D. | N.D. |

[1]expressed in log base 2
N.D. = not determined.

TABLE 9

Results of the virus neutralization test
VN titre[1]

| Group | dose (TCID$_{50}$) | vaccination chickens | weeks after booster | | weeks post | | |
|---|---|---|---|---|---|---|---|
| | | | 4 | 6 | 2 | 4 | 6 |
| 510 | $10^{8.0}$ | vaccinated | 3.9 | 4.1 | 7.9 | 8.3 | 8.3 |
| | | controls | 3 | 3 | 3 | 3 | 3 |
| 515 | $10^{9.0}$ | vaccinated | 5.0 | 5.3 | 9.2 | 10.4 | 9.6 |
| | | controls | 3 | 3 | 3 | 3 | 3 |

[1]expressed in log base 2

I claim:

1. An attenuated chicken anemia agent (CAA) virus that induces lesions in chicken embryos.

2. A virus according to claim 1, wherein the virus is of the strain I-1141 deposited with the CNCM of the Institut Pasteur.

3. A composition comprising the CAA virus according to claim 1 and a carrier.

4. A composition according to claim 3, wherein the composition comprises at least $10^{8.0}$ TCID$_{50}$ per ml.

5. A live vaccine for the protection of chickens against CAA, comprising attenuated CAA virus according to claim 1 and a carrier.

6. A vaccine for the protection of chickens against CAA, comprising an effective amount of inactivated CAA viruses, and a carrier, wherein the vaccine is capable of eliciting the production of CAA virus neutralizing antibodies in a chicken after vaccination.

7. A vaccine according to claim 6, wherein a pre-inactivation amount of the CAA virus is about $10^{7.5}$ TCID$_{50}$ or greater per dose.

8. A vaccine according to claim 7, wherein the pre-inactivation amount is at least about $10^{8.0}$ TCID$_{50}$ per dose.

9. A vaccine according to claim 6, which further contains an adjuvant.

10. A vaccine according to claim 5, wherein the vaccine further comprises antigens of at least one unrelated avian pathogen.

11. A method for the preparation of CAA virus product, comprising:

a) inoculating a susceptible substrate with the CAA virus according to claim 1, b) propagating the CAA virus, and c) harvesting CAA virus-containing material.

12. A method according to claim 11, wherein the substrate is embryonated eggs.

13. A composition comprising the CAA virus according to claim 2 and a carrier.

14. A live vaccine for the protection of chickens against CAA comprising attenuated CAA virus according to claim 2 and a carrier.

15. A vaccine according to claim 6, wherein the vaccine further comprises antigens of at least one unrelated avian pathogen.

16. A method for the preparation of CAA virus product, comprising:

a) inoculating a susceptible substrate with the CAA virus according to claim 2, b) propagating the CAA virus, and c) harvesting CAA virus-containing material.

17. A method according to claim 16, wherein the substrate is embryonated eggs.

18. A vaccine according to claim 6, wherein, prior to inactivation, said CAA viruses have the characteristic of inducing lesions in chicken embryos.

19. A vaccine according to claim 7, wherein prior to inactivation, said CAA viruses have the characteristic of inducing lesions in chicken embryos.

20. A vaccine according to claim 8, wherein, prior to inactivation, said CAA viruses have the characteristic of inducing lesions in chicken embryos.

* * * * *

UNITED STATES PATENT AND TRADEMARK OFFICE
CERTIFICATE OF CORRECTION

PATENT NO : 5,728,569
DATED : March 17, 1998
INVENTOR(S): Carla C. Schrier

It is certified that error appears in the above-identified patent and that said Letters Patent is hereby corrected as shown below:

On the title page, left hand column, in the "[*] Notice:" section, second line, please delete "2011" and replace with -- 2014 --.

Signed and Sealed this

Twenty-fifth Day of August, 1998

Attest:

*Attesting Officer*

BRUCE LEHMAN

*Commissioner of Patents and Trademarks*